US007767962B2

(12) United States Patent
Gignac et al.

(10) Patent No.: US 7,767,962 B2
(45) Date of Patent: Aug. 3, 2010

(54) METHOD FOR SEM MEASUREMENT OF FEATURES USING MAGNETICALLY FILTERED LOW LOSS ELECTRON MICROSCOPY

(75) Inventors: Lynne Gignac, Beacon, NY (US); Oliver Wells, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 378 days.

(21) Appl. No.: 11/581,498

(22) Filed: Oct. 16, 2006

(65) Prior Publication Data

US 2007/0029479 A1 Feb. 8, 2007

Related U.S. Application Data

(63) Continuation-in-part of application No. 11/518,860, filed on Sep. 11, 2006, now abandoned, which is a continuation of application No. 11/037,613, filed on Jan. 18, 2005, now Pat. No. 7,105,817.

(51) Int. Cl.
 *H01J 37/244* (2006.01)

(52) U.S. Cl. ...................................................... 250/310

(58) Field of Classification Search .................. 250/310
 See application file for complete search history.

(56) References Cited

U.S. PATENT DOCUMENTS 4,962,306 A * 10/1990 Hodgson et al. ............ 250/310
5,408,098 A * 4/1995 Wells ......................... 250/310
6,768,111 B1 * 7/2004 Wells et al. ................. 250/307

\* cited by examiner

*Primary Examiner*—Kiet T Nguyen
(74) *Attorney, Agent, or Firm*—Rodney T Hodgson

(57) ABSTRACT

A magnetically focused scanning charged particle microscope having an array detector placed to detect scattered particles, wherein the particles fall substantially non-tangentially to the surface of the array detector.

17 Claims, 3 Drawing Sheets

US 7,767,962 B2

METHOD FOR SEM MEASUREMENT OF FEATURES USING MAGNETICALLY FILTERED LOW LOSS ELECTRON MICROSCOPY

CROSS REFERENCE TO RELATED APPLICATIONS

This application is a continuation-in-part (CIP) of U.S. application Ser. No. 11/518,860 filed Sep. 11, 2006, which claims priority pursuant to 35 U.S.C. 119(e) to the U.S. application Ser. No. 11/037,613, filed Jan. 18, 2005 (now U.S. Pat. No. 7,105,817) all of the above applications being incorporated herein by reference in their entirety including incorporated material.

FIELD OF THE INVENTION

The field of the invention is the field of scanning charged particle beam microscopes.

BACKGROUND OF THE INVENTION

In a scanning electron microscope (SEM), a focused electron beam is scanned across the surface of a specimen. Signals (typically electrons) emitted from the region of the surface struck by the incident electron beam are detected, typically by a solid state diode or by a scintillator or phosphor that is optically coupled to a photomultiplier, and the current generated by the detected signal determines the current of a beam of electrons in a cathode ray tube (CRT). As the focused electron beam is scanned over the surface, an image is built up on the CRT. SEM's are well known in the art and well described, for example, in numerous publications, among the first of which is by D. McMullan entitled "An improved scanning electron microscope for opaque specimens." published in Proc. IEE vol. 100 Part II, 245-259 (1953).

A particular type of SEM is one in which the specimen is placed in the high field region of the magnetic lens of the microscope. Such microscopes are called immersion lens SEM's, and can produce better resolution for the same beam energy.

In particular, the magnetic field at the focus of an SEM can be used to energy analyze the backscattered electrons from a specimen, as explained in great detail by U.S. Pat. No. 4,962, 306 issued Oct. 9, 1990.

U.S. Pat. Nos. 7,105,817, 6,768,111, and 5,408,098 give further details of the use of SEM's in imaging and in topographical measurement. All of the above applications are hereby incorporated herein by reference in their entirety including incorporated material.

RELATED PATENTS AND APPLICATIONS

The above identified patents and patent applications are assigned to the assignee of the present invention and are incorporated herein by reference in their entirety including incorporated material.

OBJECTS OF THE INVENTION

It is an object of the invention to produce a method of using a beam of charged particle focused on a specimen in a magnetic field to produce backscattered and secondary electrons, which are analyzed by an array detector to produce images and measurements of the specimen.

SUMMARY OF THE INVENTION

An array detector detects charged particles scattered from a portion of a surface of a specimen placed in a magnetic field at a focus of the scanning charged particle microscope. The charged particles scattered from surface impinge on the array detector substantially non-tangentially to the surface of the array detector.

DETAILED DESCRIPTION OF THE INVENTION

A charged particle beam microscope generates a beam of electrons or ions and focuses the charged particle beam on the surface of a specimen. A preferred embodiment of the invention uses a beam of ions to probe the surface. Preferred ions are protons, deuterons, or helium ions. Other preferred ions are cesium ions and argon ions. The most preferred embodiment of the invention uses a beam of electrons to probe the surface of the specimen.

Electrons emitted from the surface are captured and used to construct an image of the surface or a topographical map of the surface. The image contrasts that are shown in a backscattered electron (BSE) image in the SEM will depend on the tilt angle of the specimen, the incident beam energy, the energy sensitivity of the BSE detector, the position of the BSE detector relative to the sample and the incident electron beam and other factors. In particular, the electrons which have lost the least energy are the electrons which are emitted from the surface or from a very shallow depth into the surface of the specimen, as the electrons lose energy at a constant rate as they move through the material of the specimen. Thus, the lowest energy loss backscattered electrons give a unique picture of the surface of the specimens.

A particular type of SEM is one in which the specimen is placed in a magnetic lens of the SEM. Such microscopes are called immersion lens SEM's, and can produce better resolution for the same beam energy.

In particular, the magnetic field at the focus of an SEM can be used to energy analyze the backscattered electrons from a specimen, as explained in great detail by U.S. Pat. No. 4,962, 306 issued Oct. 9, 1990.

Figure 1A:
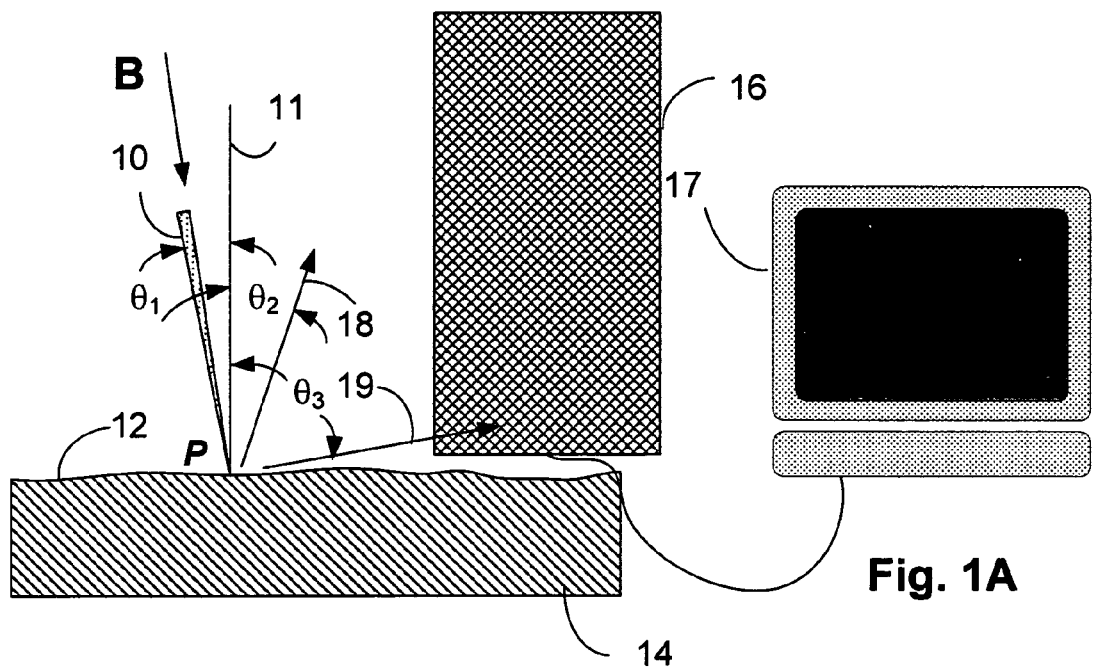
FIG. 1A shows an elevation sketch of the apparatus of the invention.

The sketch of the of the invention is shown in side elevation FIG. 1. A focused electron beam 10 is shown propagating parallel to magnetic field B and incident on a surface 12 of a specimen 14. Electron beam 10 forms an angle $\theta_1$ with respect to the average normal to the surface 11. Electrons 18 and 19 are shown leaving the point of intersection of the electron beam 10 and the surface 12 with angles $\theta_2$ and $\theta_3$ with respect to the normal 11 to the surface respectively. The electrons spiral away from the surface with constant velocity component parallel to the magnetic field. If the magnetic field is uniform, in plan view, the electrons travel in circles in the magnetic field. For the typical case that the magnetic field is not uniform, the radius of the circular arc changes as the electrons move further from the starting point. Typical curves were published by O. C. Wells and E. Munro in "Magnetically filtered low loss scanning electron microscopy", Ultramicroscopy 47, (101-108 (1992).

The electron detecting array device 16 required for the method of the invention is shown in side elevation intercepting electrons 18 and 19. Images constructed from signals from imaging device 16 are displayed on display device 17.

Figure 1B:
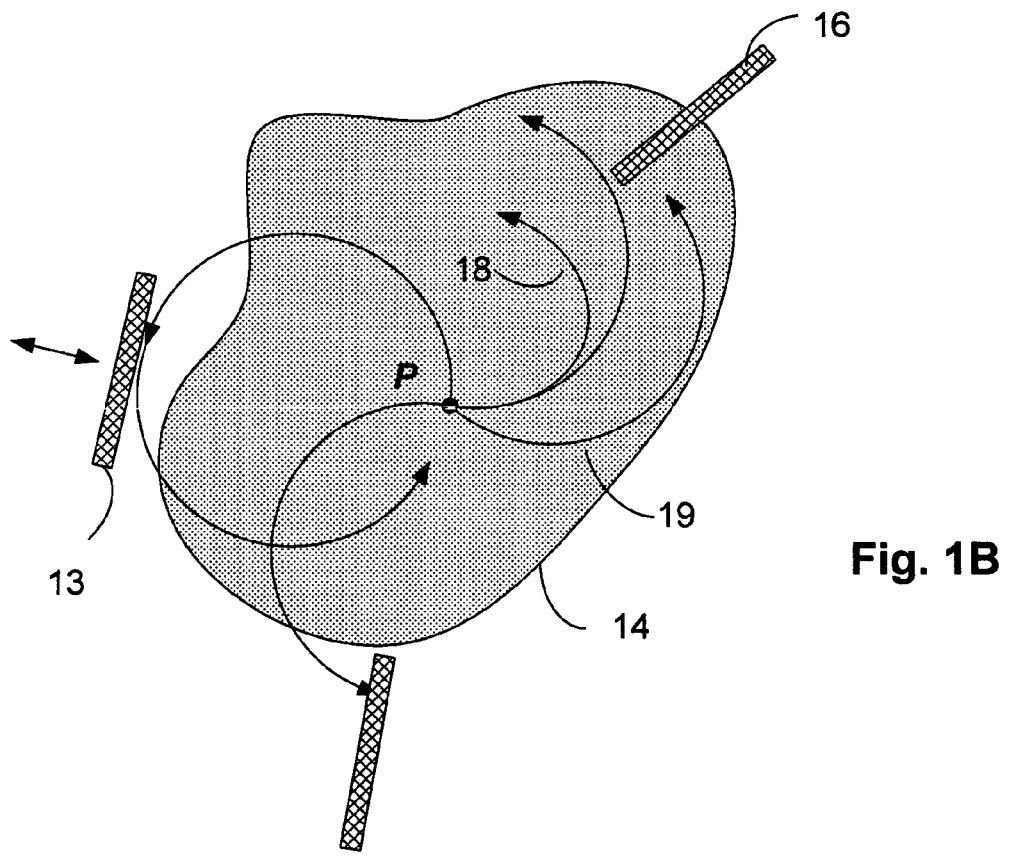
FIG. 1B shows a plan sketch of the apparatus of the invention.

FIG. 1B shows a sketch of the apparatus of the invention in plan view looking along the direction of the magnetic field B. Electrons emitted from the surface of the specimen travel in spiral paths about the magnetic field lines. Electrons 19 are shown impinging on the array detector 16 substantially normal to the surface of the detector 16. Detector 13 is shown detecting electrons which impinge on the detector substantially tangential to the surface of detector 13. If the surface of detector 16 is in a plane which includes the focal point P of the beam 10, electrons which are emitted horizontally and normal to the plane of the detector from point P will impinge on the detector normally after completing a half circle. Electrons 15 and 19a are shown as examples of electrons which are emitted from the surface 12 with the same direction, but different energies, or as examples of electrons which are emitted from the surface with the same energy, but with different angles ($\theta_1 + \theta_2$) to the direction of the field B.

Figure 2:
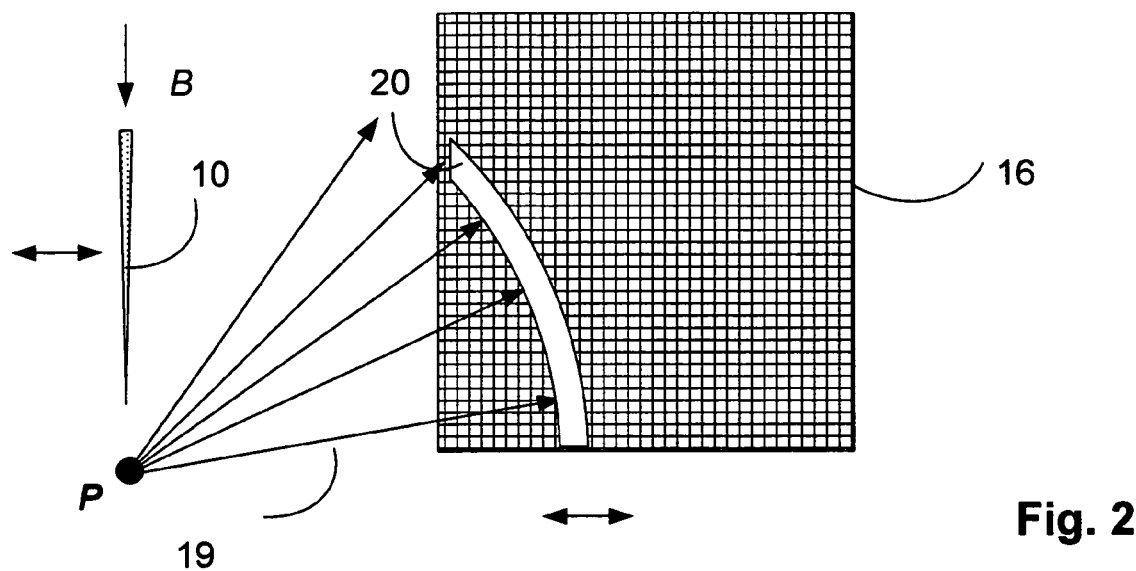
FIG. 2 shows an elevation sketch of electron trajectories of the invention.

FIG. 2 shows an elevation view of a number of electron trajectories which start with the same energy at the same point and the same direction in the plane perpendicular to the field B. and have different angles with respect to the field B. These electrons land on the array detector 16 in a non circular arc 20. As the beam 10 and the detector 16 move relativly with respect to one another to scan the specimen as noted by the double headed arrows, the arc 20 will move back and forth on the detector array 16 in a predictable way. The signals from equal energy electrons as the beam scans must then be determined from different detection elements of detector 16 during the scan, and these signals may be used to construct an image of the surface 12. In particular, the preferred image that can be so constructed is the low loss image, where the electrons which have lost the least energy in scattering from the surface are used to produce the image.

Figure 3:
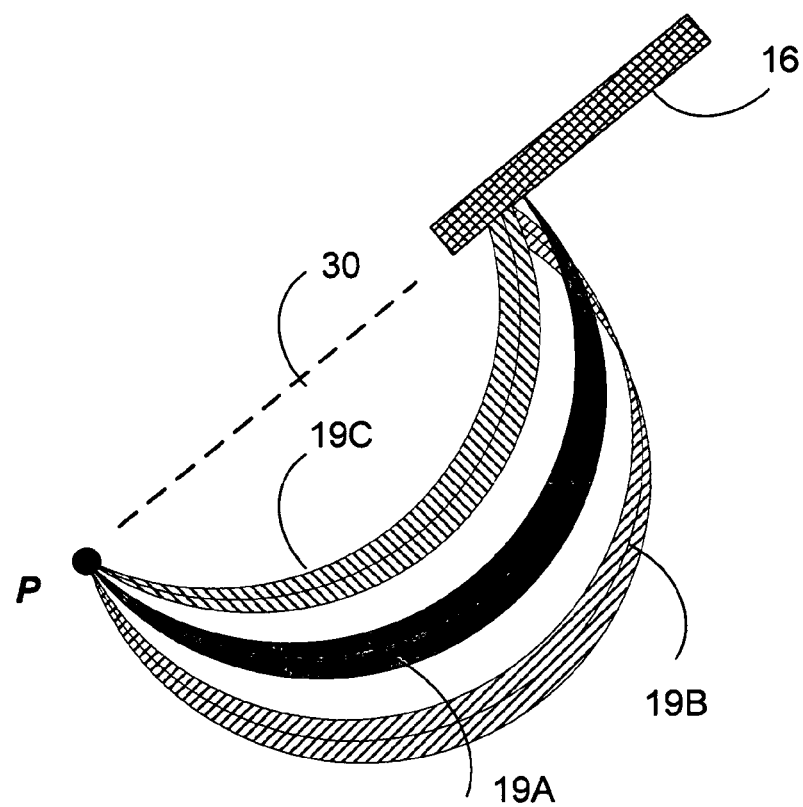
FIG. 3 shows a plan sketch of electron trajectories of the invention.

FIG. 3 shows a plan view of a number of bands of electron trajectories which start with the same energy at the same point with the same angles with respect to the field B but in different directions in the plane perpendicular to the field B. Electrons 19A which start with a horizontal component nearly perpendicular to the plane of the surface of detector 16 are focused to a small area on detector 16, whereas electrons 19B and 19C which start with horizontal components in different directions from the perpendicular "focus" before or after detector 16 and land on detector 16 closer to point P than the landing point of electrons 19A.

Electrons which have horizontal components component nearly perpendicular to the plane 30 of the surface of detector 16 but with different angles with respect to the field B are focused into a thin line on detector 16 as shown in FIG. 2A. The signal from the pixels excited by electrons 19A can be used to calculate expected signals from low loss electrons such as 19B and 19C which land in broader "lines" closer to point P than the electrons 19A. The contribution from succeeding sets of higher energy loss electrons (not shown) can be estimated by subtracting the signals from the lower energy loss electrons which land on the same pixels.

Figure 4A:
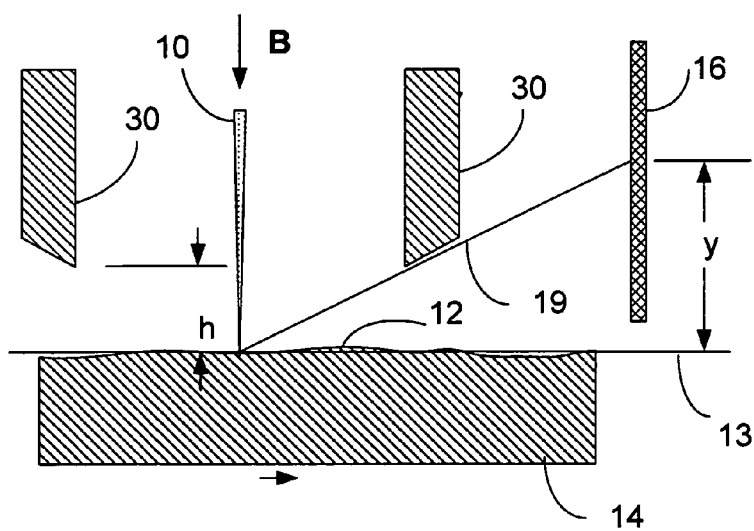
FIG. 4 shows an elevation sketch of a preferred embodiment of the invention.
Figure 4B:
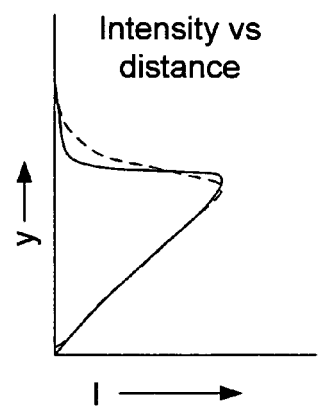

The method of the invention is also used to construct a topographic image of the surface of the specimen 12 by either using features on the surface of the specimen or an electron opaque material spaced apart from the surface of the specimen. FIG. 4A shows an elevation view of the sketch of the with an electron opaque material 30 interposed between the surface 12 and the detector 16. As the surface 12 varies in height, the shadow of the electron opaque material 30 moves up and down on the detector. The topography of the surface can then be reconstructed by the shadow line as detailed in the cited US patents. In addition, the topographic features of the surface 12 can also be used to shadow the electrons 19.

The electron imaging device 16 has a large plurality of individual detector elements, preferably 9 individual detector elements, more preferably 16 individual element, and most preferably at least 256 elements. For the purposes of this specification, a large plurality of individual detector elements is defined as 9 elements or greater. Electron imaging devices of 1024 elements and up to millions of individual elements are currently available. The signals from a number of individual detector elements may be binned together in regions. The signals from such individual detector elements or combinations of elements may be used to construct and display an image of the surface 12 on a display device as the electron beam 10 is scanned over the surface, or to construct and display a plurality of images of the surface taken with, for example, low energy loss electrons and higher energy loss electrons.

Using the apparatus of the invention, the method of measurement of features on a surface of a specimen, comprises:
a) directing a focused beam of charged particles to fall on to a portion of the surface of the specimen, wherein the surface of the specimen is immersed in a magnetic lens of a magnetically focused scanning charged particle microscope;
b) detecting charged particles emitted from the portion of the surface of the specimen with at least one array detector, wherein the charged particles emitted from the portion of the surface impinge on the array detector substantially non-tangentially to the surface of the array detector;
c) determining the energy of the charged particles impinging on detector elements in the detector array;
d) constructing an image of the portion of the surface of the specimen from signals produced by the charged particles impinging on the detector elements as the focused beam of charged particles is scanned over the first portion of the surface of the specimen.

Obviously, many modifications and variations of the present invention are possible in light of the above teachings. It is therefore to be understood that, within the scope of the appended claims, the invention may be practiced otherwise than as specifically described.

We claim:
1. An apparatus, comprising:
a scanning charged particle microscope; and
at least one array detector for detecting charged particles scattered from a portion of a surface of a specimen, wherein the portion of the surface is placed in a magnetic field at a focus of the scanning charged particle microscope, and wherein the charged particles scattered from the portion of the surface impinge on the array detector substantially non-tangentially to the surface of the array detector.

2. The apparatus of claim 1, wherein the scanning charged particle microscope is a scanning electron microscope (SEM).

3. The apparatus of claim 2, wherein at least two array detectors are inserted into the path of the charged particles emitted from the portion of the surface scattered from the specimen in the magnetic field.

4. The apparatus of claim 2, further comprising an electron opaque material located between the portion of the surface of the specimen and the array detector, wherein the electron opaque material blocks electrons which scatter from the portion of the surface at defined angles with respect to the normal to the portion of the surface of the specimen.

5. The apparatus of claim 4, wherein the electron opaque material is a part of the surface of the specimen.

6. The apparatus of claim 4, wherein the electron opaque material is spaced apart from the surface of the specimen.

7. A method of measurement of features on a surface of a specimen, comprising:
   a) directing a focused beam of charged particles to fall on to a portion of the surface of the specimen, wherein the surface of the specimen is immersed in a magnetic lens of a magnetically focused scanning charged particle microscope;
   b) detecting charged particles emitted from the portion of the surface of the specimen with at least one array detector, wherein the charged particles emitted from the portion of the surface impinge on the array detector substantially non-tangentially to the surface of the array detector;
   c) determining the energy of the charged particles emitted from the portion of the surface impinging on detector elements in the detector array; and
   d) constructing an image of the portion of the surface of the specimen from signals produced by the charged particles impinging on the detector elements as the focused beam of charged particles is scanned over the portion of the surface of the specimen.

8. The method of claim 7 wherein a plurality of array detectors is used to detect the scattered charged particles emitted from the portion of the surface.

9. The method of claim 7, wherein charged particles emitted from the portion of the surface having the same scattering angle with respect to the normal to the portion of the surface and the same scattering direction and suffering the same lowest energy loss in scattering impinge on different individual elements of the detector array during the time that the focused beam of charged particles is scanned over the portion of the surface of the specimen, and
   wherein in step c) signals from different detector elements are used to detect the lowest energy loss charged particles emitted from the portion of the surface are used to construct the image as the focused beam of charged particles is scanned over the portion of the surface of the specimen.

10. The method of claim 7, wherein an electron opaque material between the portion of the surface of the specimen and the array detector blocks electrons emitted from the portion of the surface at defined angles with respect to the normal to the portion of the surface of the specimen.

11. The method of claim 10, wherein the electron opaque material is a part of the surface of the specimen.

12. The apparatus of claim 11, wherein the electron opaque material is spaced apart from the surface of the specimen.

13. A method of measurement of features on a surface of a specimen, comprising:
in a magnetic field at a focus of a scanning charged particle microscope
   a) directing a focused beam of electrons to fall on to a first portion of the surface of the specimen, wherein the surface of the specimen is immersed in a magnetic field at a focus of a magnetically filtered low loss scanning electron microscope (SEM);
   b) detecting magnetically filtered electrons emitted from the first portion of the surface of the specimen with at least one array detector, wherein the magnetically filtered electrons impinge substantially non-tangentially on to the surface of the at least one array detector;
   c) determining the energy of the magnetically filtered electrons impinging on detector elements in the detector array;
   d) constructing an image of the first portion of the surface of the specimen from signals produced by the magnetically filtered electrons impinging on the detector elements as the focused beam of electrons is scanned over the first portion of the surface of the specimen.

14. The method of claim 13, further comprising;
   e) determining the topographic features of the plurality of portions of the surface from the results of the detection of electrons.

15. The method of claim 14, wherein an electron opaque material between the portion of the surface of the specimen and the array detector blocks electrons emitted from the portion of the surface at defined angles with respect to the normal to the portion of the surface of the specimen.

16. The method of claim 15, wherein the electron opaque material is a part of the surface of the specimen.

17. The method of claim 15, wherein the electron opaque material is spaced apart from the surface of the specimen.

* * * * *